United States Patent [19]

Haynes

[11] Patent Number: 5,306,235
[45] Date of Patent: Apr. 26, 1994

[54] FAILSAFE IONTOPHORESIS DRUG DELIVERY SYSTEM

[75] Inventor: John L. Haynes, Chapel Hill, N.C.

[73] Assignee: Becton Dickinson and Company, Franklin Lakes, N.J.

[21] Appl. No.: 954,176

[22] Filed: Sep. 30, 1992

[51] Int. Cl.$^5$ .............................................. A61N 1/30
[52] U.S. Cl. ...................................... 604/20; 607/149
[58] Field of Search ............... 128/798, 802, 803, 898; 604/70, 49; 607/149, 151

[56] References Cited

U.S. PATENT DOCUMENTS

| | | | |
|---|---|---|---|
| 4,141,359 | 2/1979 | Jacobsen et al. | 604/20 |
| 4,292,968 | 10/1981 | Ellis | 604/20 |
| 4,456,012 | 6/1984 | Lattin | 604/20 |
| 4,764,164 | 8/1988 | Sasaki | 604/20 |
| 5,047,007 | 9/1991 | McNichols et al. | 604/20 |

OTHER PUBLICATIONS

Application notes of Maxim Company, pp. 1-19 to 1-20, undated.

Primary Examiner—C. Fred Rosenbaum
Assistant Examiner—Michael Rafa
Attorney, Agent, or Firm—Hoffmann & Baron

[57] ABSTRACT

An iontophoresis system includes an iontophoretic drug delivery device for placement against the skin of a patient and having a pair of electrodes, and a circuit for delivering and controlling the current and voltage provided to the electrodes. The current and voltage controlling circuit includes a power supply for generating a voltage or current, an intermediary storage device and a first switching circuit interposed and coupled to the power supply and the intermediary storage device. The intermediary storage device is selectively coupled to the drug delivery device through a second switching circuit or device. Energy from the power supply is transferred and stored in the intermediary storage device for later delivery to the transdermal drug delivery device. In this way, should a component of the circuit fail, the energy or power delivered to the drug delivery device is interrupted or maintained at least equal to a predetermined safe level to avoid damage or injury to the patient's skin.

19 Claims, 6 Drawing Sheets

FAILSAFE IONTOPHORESIS DRUG DELIVERY SYSTEM

BACKGROUND OF THE INVENTION

1. Field of the Invention

The present invention relates to iontophoretic devices for delivering a drug or medicant to a patient transdermally, i.e., through the patient's skin, and more specifically relates to an iontophoresis drug delivery system and circuit therefor which limits the current or voltage provided to the patient's skin to a safe level should a component of the circuit fail.

2. Description of the Prior Art

Iontophoresis can be defined as the electrically driven application of drugs or medicants, in their ionic form, to the surface tissues of a patient. The application of electric current causes migration of ions into the tissue wherein such migration is proportional to the quantity of current applied through the iontophoretic system.

One of the major drawbacks of iontophoresis is skin irritation or burns which can occur due to high current levels. It is known that the impedance of a patient's skin can range from over 100,000 ohms to nearly 1,000 ohms, depending on the duration that the iontophoretic current is applied, the magnitude of the current which is being delivered, the location of the system on the patient's body, and other factors. In a system where the desired current level, which is determined in part by the drug administered to the patient, is 1 milliamp, a voltage potential of 100 volts would result if the skin impedance is 100,000 ohms. Such a voltage would cause undesirable sensations to the user.

Numerous attempts have been made to control the amount of current or voltage provided to a patient during iontophoresis. For example, U.S. Pat. No. 4,292,968 to Ellis discloses an apparatus for delivering constant current during ion therapy (iontophoresis) which will abruptly switch to delivering constant voltage when the voltage across the electrodes of the drug delivery device reaches a predetermined level. The circuit disclosed in the Ellis patent includes a voltage limiter 14 which is provided in shunt with the electrodes of the device for limiting the output voltage across the electrodes. The Ellis patent describes the voltage limiter 14 as functioning as a variable resistive path shunting the electrodes. When the electrode voltage is less than a predetermined voltage, the limiter 14 is stated to present a high resistance and all the current generated by the circuit is provided to the electrodes. However, when the voltage across the electrodes reaches the predetermined voltage, the resistance of the limiter 14 is stated to drop, drawing current that would have been provided to the electrodes.

One of the major disadvantages of the circuit described in the Ellis patent is that it is not failsafe. Should certain of the components of the circuit fail, it is possible for the Ellis circuit to deliver excessive current to the patient, causing skin irritation or tissue damage. For example, if the voltage limiter 14 failed such that it no longer acted as a variable resistor or no longer shunted the electrodes of the device, no voltage regulation would occur when the predetermined voltage across the electrodes is reached. The voltage across the electrodes could reach dangerous levels, resulting in skin burns or tissue damage.

Another iontophoresis device is disclosed in U.S. Pat. No. 4,141,359 to Jacobsen, et al. The Jacobsen, et al. patent discloses an epidermal iontophoresis device which is stated to be capable of maintaining a constant current through the epidermal tissue. To prevent excessive voltage build-up and the accompanying dangers of shock and burns, a comparator circuit monitors current flow and voltage across the electrodes of the device and automatically triggers an SCR shut down circuit when impedance readings are outside of predetermined limits.

As with the circuit disclosed in the Ellis patent, the iontophoresis device described in the Jacobsen, et al. patent is not safe if certain components fail. For example, if the SCR fails and becomes effectively an open circuit, it will no longer be capable of de-energizing the current source used in the circuit, resulting in burns, shocks and other dangerous effects of excessive current and voltage.

OBJECTS AND SUMMARY OF THE INVENTION

It is an object of the present invention to provide an iontophoresis system having failsafe capability to prevent excessive current or voltage from being provided to a patient during transdermal drug delivery should a component of the system fail.

It is another object of the present invention to provide an iontophoresis drug delivery system which has an inherent power limitation which limits the power delivered to a patient undergoing transdermal drug delivery.

It is yet another object of the present invention to provide a circuit for use in an iontophoresis system and for connection to a transdermal drug delivery device, which circuit is inherently power limiting and/or failsafe such that, if certain components of the circuit fail, no excessive current or voltage is provided to the patient undergoing iontophoresis.

It is a further object of the present invention to provide an iontophoresis system and method which overcomes the inherent disadvantages of known systems and methods.

In accordance with one form of the present invention, a failsafe iontophoresis drug delivery system includes an iontophoretic drug delivery device for placement against the skin of a patient, and a failsafe circuit for controlling current or voltage provided to the drug delivery device. More specifically, the iontophoretic drug delivery device of the system includes a first electrode, which may act as a cathode, and a container or other structure for holding an electrolyte situated in relation to the first electrode such that the electrolyte is in electrical communication with the first electrode. The drug delivery device also includes a second electrode, which may act as an anode, and a container or other structure for holding an ionic medication situated in relation to the second electrode such that the medication is in electrical communication with the second electrode.

The failsafe circuit for controlling current or voltage provided to the first and second electrodes includes a power supply, for example, a constant current source or a constant voltage source. The circuit also includes an intermediary storage circuit or device. The storage device is selectively coupled by way of a first switching circuit or the like to the power supply. The intermediary storage device is also selectively coupled, by a second switching circuit, device or the like, to the electrodes of the drug delivery device.

The intermediary storage circuit or device may be, for example, a capacitor or inductor circuit, which is capable of storing energy when connected to the power supply. A control circuit may be used to open or close the first switching circuit, so that energy may be transferred to and stored in the intermediary storage device, and may be used to control the second switching circuit, if such is included, to allow energy stored in the storage device to be transferred to the drug delivery device.

The failsafe iontophoresis system and circuit of the present invention only allows energy stored in the storage device to be transferred to the electrodes of the transdermal drug delivery device. The circuit will not allow the power supply to be connected directly to the electrodes and, even more preferably, if one of the components should fail in the circuit of the iontophoresis system, the voltage or current provided to the electrodes will either be zero or be limited to a predetermined safe voltage and current.

These and other objects, features and advantages of the present invention will become apparent from the following detailed description of illustrative embodiments thereof, which is to be read in connection with the accompanying drawings.

DETAILED DESCRIPTION OF THE PREFERRED EMBODIMENTS

Figure 1:
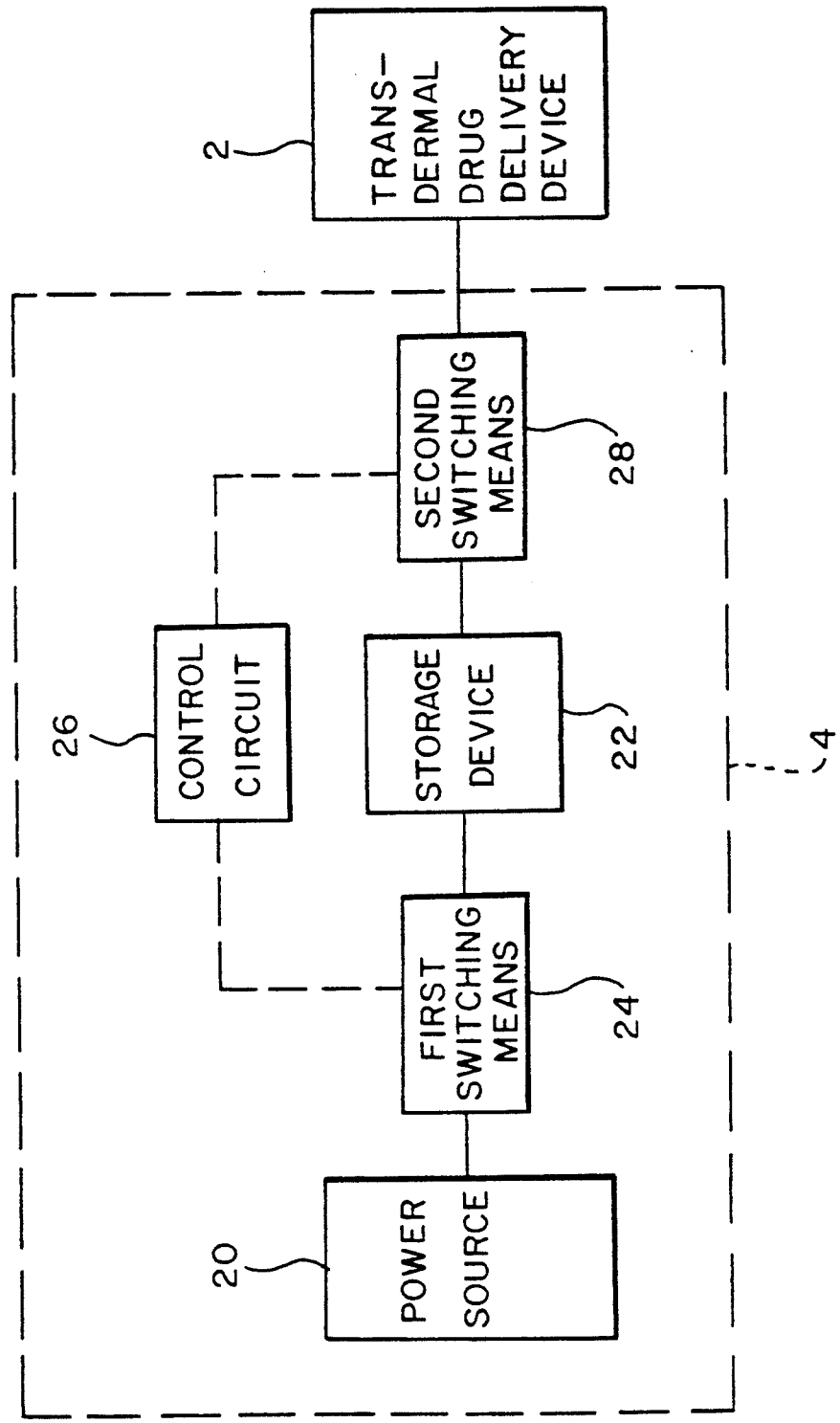
FIG. 1 is a block diagram of an iontophoresis system formed in accordance with one form of the present invention.

Referring initially to FIG. 1 of the drawings, it will be seen that an iontophoresis system for delivering ionic medication to a patient transdermally, that is, through the skin of the patient, basically includes a transdermal drug delivery device 2 for placement against the skin of the patient, and a circuit 4 for controlling the current and voltage provided to the drug delivery device.

Figure 2:
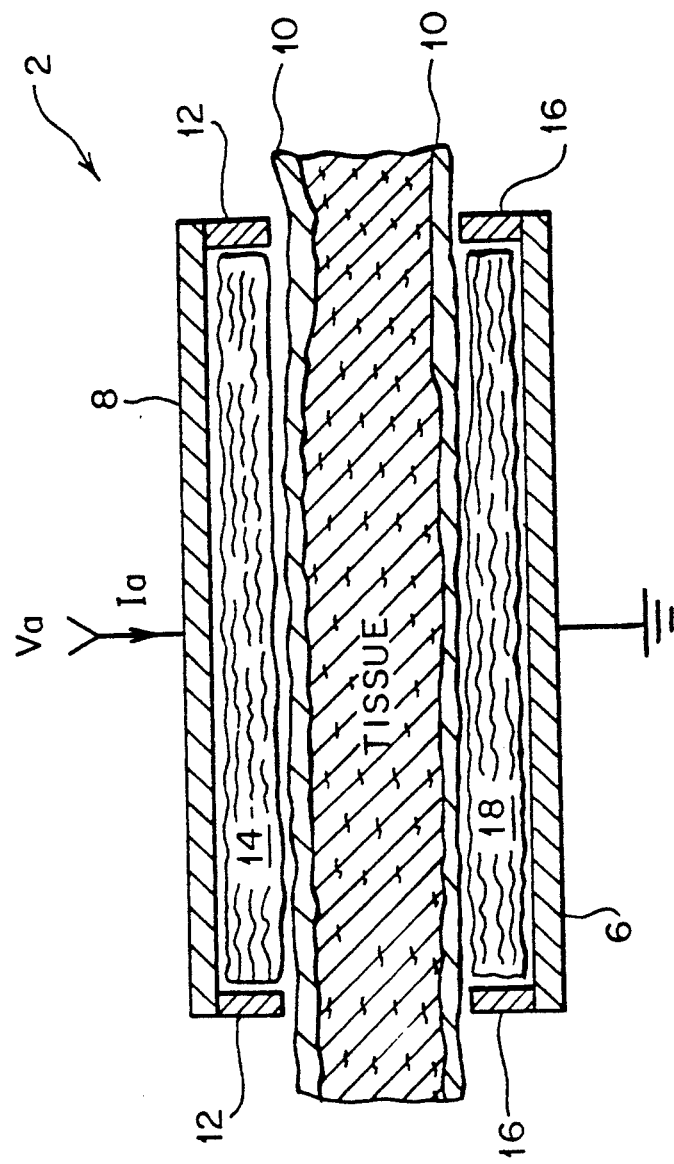
FIG. 2 is a cross-sectional view of a portion of the iontophoresis system of the present invention shown in FIG. 1.

One form of a transdermal drug delivery device 2 is illustrated by FIG. 2. The transdermal drug delivery device basically includes a first electrode 6, which may act as a cathode, and a second electrode 8, which may act as an anode. The transdermal drug delivery device 2 is placeable against the skin 10 of a patient so that the anode electrode 8 and cathode electrode 6 are in electrical communication with the patient's skin.

Adjacent to the anode (i.e., the second electrode 8) is a container or other suitable structure 12 defining a well for holding an ionic medication 14 in place between the anode and the skin of the patient. Similarly, adjacent to the cathode (i.e., the first electrode 6) is a container or other suitable structure 16 forming a well for holding an electrolyte 18 in place between the cathode and the skin of the patient.

When a voltage $V_a$ is impressed across the first and second electrodes 6, 8, current $I_a$ will flow through the skin of the patient, driving the ionic medication into the skin and tissue to be absorbed by the patient's body.

Referring again to FIG. 1 of the drawings, the iontophoresis system of the present invention also includes a current or voltage delivery circuit 4 which controls the current passing through each of the electrodes 6,8 and the voltage across the electrodes. The current and voltage delivery circuit 4 basically includes a power source or supply 20, which may be a constant current source or a constant voltage source. The circuit also includes an intermediary storage device or circuit 22. In one form of the present invention, the intermediary storage device may be a capacitor or inductor circuit, as will be described in greater detail. Energy from the power source 20 will be transferred to and stored in the intermediary storage device 22 for later delivery to the transdermal drug delivery device 2.

The intermediary storage device 22 is selectively coupled to the power source 20 through first switching means 24. The first switching means 24, which is interposed between the power supply and the intermediary storage device, may be in the form of an electronic switch, field effect transistor (FET) or the like, to selectively interrupt the connection between the power supply 20 and the intermediary storage device 22.

A control circuit 26 is coupled to the first switching means 24 and is used to activate the first switching means to selectively open and close the connection between the power supply 20 and the intermediary storage device 22. The control circuit 26 may be any one of a number of suitable circuits which may be used, such as an astable multivibrator which provides an output control signal to the first switching means 24 having a predetermined duty cycle and frequency to control the operation of the first switching means.

When the first switching means 24 is in one state (i.e., a conductive state), the power supply output is coupled to the intermediary storage device 22 so that energy generated by the power supply 20 may be transferred to the intermediary storage device and stored therein. When the first switching means 24 is in a second state (i.e., a non-conductive state), the intermediary storage device 22 is disconnected from the power supply 20 so that no additional energy is stored in the intermediary storage device. The quantity of energy transferred to and stored in the intermediary storage device 22 may be controlled by the control circuit 26 and the parameters of the current or voltage source selected as the power supply 20.

The current and voltage delivery circuit 4 of the iontophoresis system also includes second switching means 28. The second switching means 28 is interposed between the output of the intermediary storage device 22 and the transdermal drug delivery device 2. The second switching means 28 has a conductive and a non-conductive state. When the second switching means is in the conductive state, the intermediary storage device 22 is effectively coupled to the transdermal drug delivery device 2 so that energy stored in the intermediary storage device may be transferred to the drug delivery device. When the second switching means 28 is in the non-conductive state, the intermediary storage device 22 is effectively decoupled from the transdermal drug delivery device and no energy is transferred.

In one form of the present invention, the second switching means 28 may be a switch circuit or the like, similar to the first switching means, and controlled to become conductive or non-conductive by the control circuit 26. The second switching means may also be a diode circuit or the like, as will be described in greater detail.

The iontophoresis system of the present invention shown in FIG. 1 of the drawings operates in the following manner. Energy generated by the power supply 20 is transferred to the intermediary storage device 22 and stored therein when the control circuit 26 causes the first switching means 24 to become conductive so that the power supply is effectively coupled to the intermediary storage device. During energy storage, the intermediary storage device is effectively decoupled by the second switching means 28 from the transdermal drug delivery device 2. The control circuit 26 then causes the first switching means 24 to become non-conductive, effectively decoupling the power supply 20 from the intermediary storage device 22 so that no more energy is transferred to and stored in the storage device. Accordingly, only a predetermined amount of energy is stored in the intermediary storage device for later transfer to the transdermal delivery device. The second switching means 28 now becomes conductive, effectively coupling the intermediary storage device 22 to the transdermal drug delivery device 2 so that the energy or power stored in the storage device may be transferred in the form of a voltage and current to the electrodes 6, 8 of the transdermal drug delivery device, causing the ionic medication to be driven into the skin and tissue to be absorbed by the patient's body.

One of the advantages of having an intermediary storage device 22 positioned between the power supply 20 and the transdermal drug delivery device 2 is that only a predetermined amount of energy is transferred to the intermediary storage device. The power supply is not normally directly coupled to the transdermal drug delivery device and so, if a component fails, the voltage or current provided to the electrodes 6, 8 of the drug delivery device will decrease to zero or to a predetermined safe level so as not to cause injury to the patient undergoing iontophoresis. There is no normal direct connection between the power supply 20 and the drug delivery device 2.

Only the predetermined amount of energy, stored in the storage device 22, is provided to the electrodes of the transdermal drug delivery device 2 in the form of a voltage or current. A power supply would effectively have unlimited energy to transfer. However, the intermediary storage device 22 only has a quantified packet of energy to deliver to the drug delivery device and no more. Accordingly, there is greater control of the power provided to the drug delivery device connected to the patient in the event of a failure, as only that energy stored in the intermediary storage device or a predetermined safe level is delivered to the transdermal drug delivery device 2.

Figure 3:
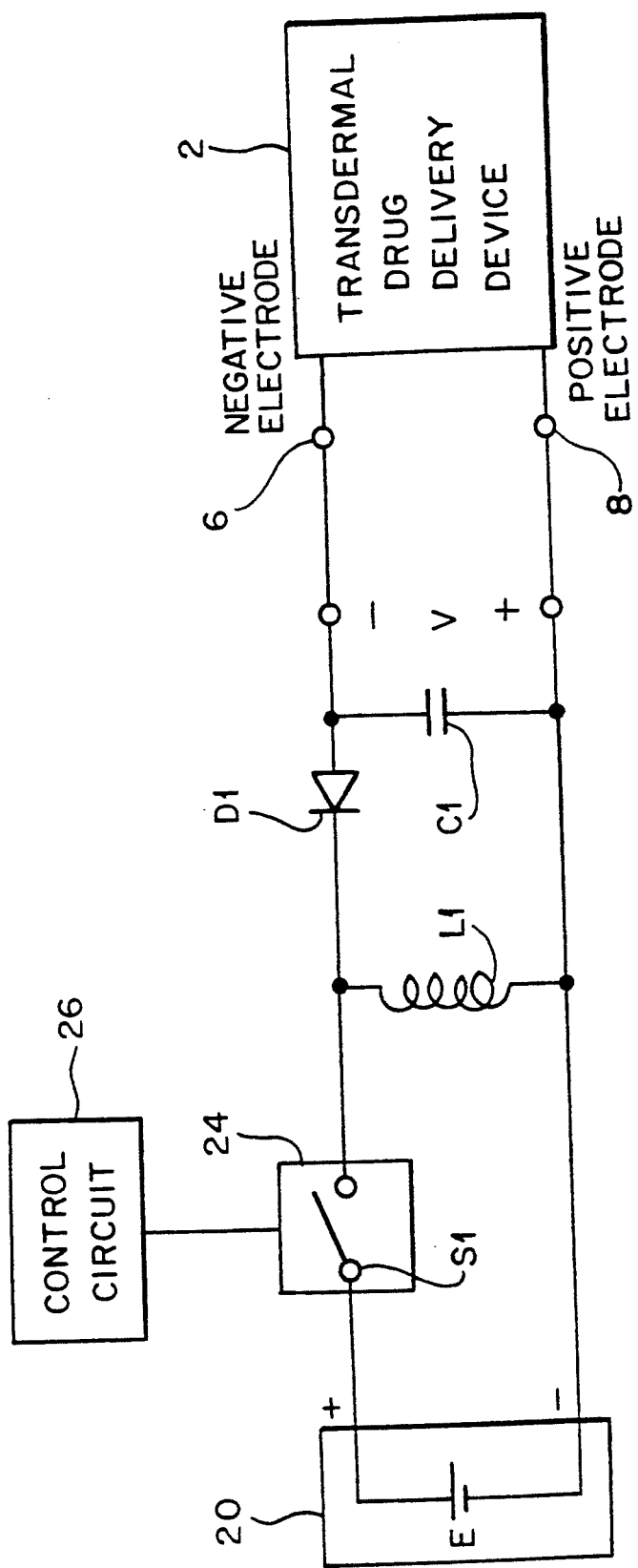
FIG. 3 is a schematic diagram of one form of an iontophoresis system formed in accordance with the present invention and shown in block diagram form in FIG. 1.

A preferred form of the iontophoresis system of the present invention is shown in FIG. 3 of the drawings. The current and voltage delivery circuit 4 shown in FIG. 3 and which is connected to the transdermal drug delivery device 2 is what is commonly referred to as a buck-boost circuit.

The power supply 20 generates a voltage E which is provided across an inductor L1, which acts as the intermediary storage device 22, when an electronically controlled single pole, single throw switch S1 (which acts as the first switching means 24) is activated to be conductive by the control circuit 26. The energy from the power supply 20 is transferred to and stored in the inductor L1.

A diode D1 is used as the second switching means 28. The diode D1 has its cathode connected to the inductor L1 on the positive side of the power supply 20, and its anode connected to the negative (cathode) electrode 6 of the transdermal drug delivery device. The other end of the inductor L1 and the negative output of the power supply are coupled to the positive (anode) electrode 8. While the energy is being transferred from the power supply 20 to the inductor L1, the diode D1 is back biased and no current or voltage is provided to the electrodes of the transdermal drug delivery device. After the energy has been transferred to the inductor, the control circuit 26 causes switch S1 (i.e., the first switching means 24) to open. The field induced by the voltage impressed across the inductor L1 collapses, causing a current to flow and forward biasing the diode D1. The forward biased diode allows a current to flow through the electrodes 6, 8 and a voltage V to be impressed across the electrodes of the transdermal drug delivery device 2 until all or part of the energy which had been stored in the inductor has been dissipated. After the inductor L1 has discharged, current will cease flowing through the electrodes of the drug delivery device.

In a preferred form of the buck-boost circuit shown in FIG. 3, a capacitor C1 may be coupled in parallel with the positive and negative electrodes 8, 6 of the transdermal drug delivery device 2. The capacitor C1 serves the purpose of filtering ripple on the output voltage V and to prevent voltage transients across the electrodes of the drug delivery device.

The advantage of the iontophoresis system and circuit shown in FIG. 3 is that, if any component fails, no voltage or current or a predetermined safe level of voltage or current will be delivered to the electrodes of the transdermal drug delivery device. For example, if the capacitor C1 should short, the voltage V across the electrodes of the transdermal drug delivery device 2 will become zero. If the capacitor C1 becomes an open circuit due to failure, it will have no major effect on the circuit except for a loss of filtering and the circuit will operate normally.

If the diode D1 fails and becomes an open circuit, the transdermal drug delivery device 2 is disconnected from the inductor L1 and the power supply. If the diode shorts, the output voltage V on the electrodes will be effectively equal to the reverse of the power supply voltage $-E$ volts when the first switching means 24 (i.e., switch S1) closes, and will be equal to V volts when the first switching means 24 opens and the inductor discharges. Accordingly, the average voltage supplied to the electrodes will be at a predetermined safe level between $-E$ and V volts.

If the inductor L1 fails and appears as an open circuit, no current and voltage is provided to the electrodes of the drug delivery device 2, as current is blocked by the back biased diode D1. If the inductor shorts, the voltage across the electrodes and the current provided to the electrodes will become zero, as whatever charge remains in the capacitor C1 will dissipate.

If the first switching means 24 (i.e., switch S1) should fail and appear as a short circuit, no energy will be transferred to the transdermal drug delivery device 2, as the inductor L1 appears as a short circuit when fully charged. The current into the inductor ramps up to its limit and the inductor remains charged, as it cannot transfer its energy to the drug delivery device. Of course, if the switch S1 fails as an open circuit, no voltage or current will be delivered to the electrodes of the drug delivery device.

Figure 4:
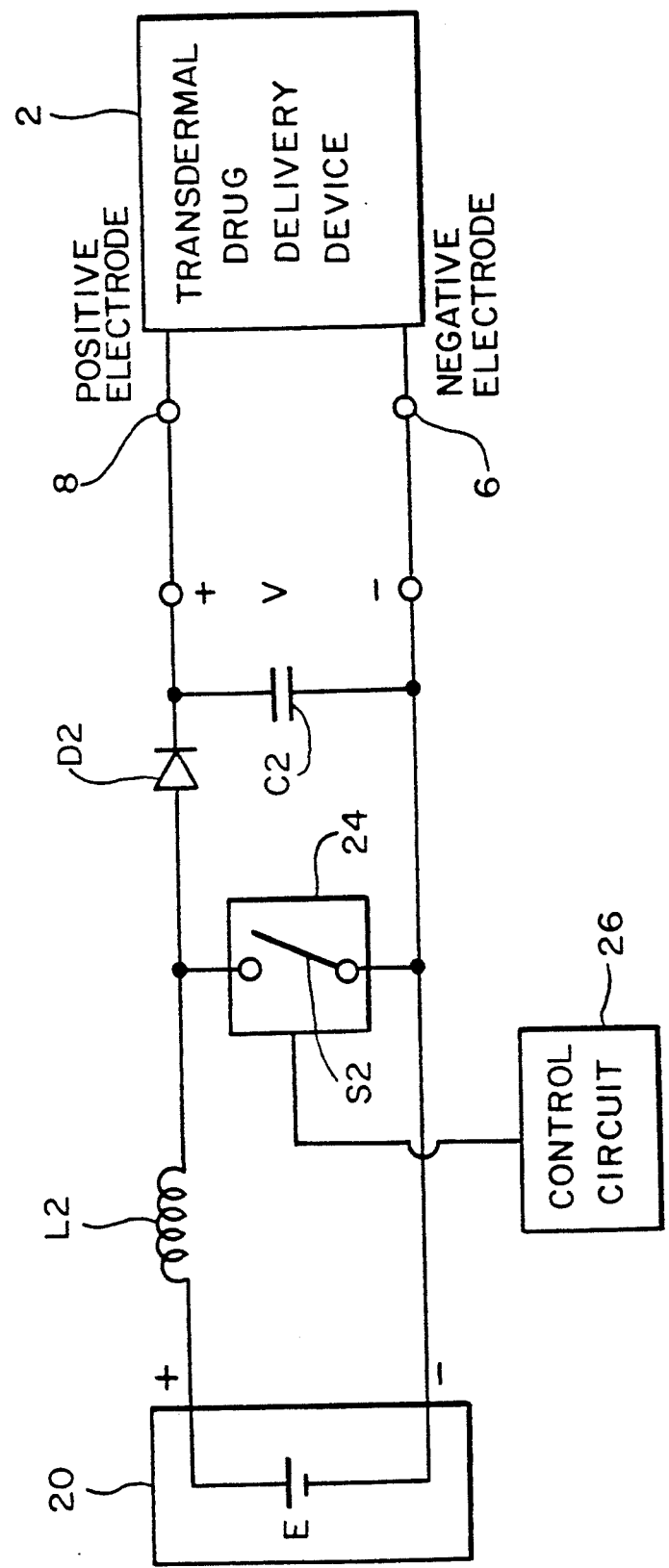
FIG. 4 is a schematic diagram of a second embodiment of an iontophoresis system formed in accordance with the present invention.

FIG. 4 illustrates a second embodiment of the iontophoresis system of the present invention. The circuit shown schematically in FIG. 4 is commonly known as a "boost" circuit or a "step-up converter." In a boost circuit, the voltage E generated by the power supply 20 is usually much less than the voltage V generated on the output of the circuit and, in the present invention, provided to the electrodes 6, 8 of the transdermal drug delivery device. In effect, the circuit increases or "boosts" the power supply voltage E to some usable output voltage V. The output voltage of the power supply may be relatively low and determined to be a safe level, and the output voltage V provided to the electrodes of the transdermal drug delivery device 2 may be at a higher level to drive the ionic medication into the skin and tissue of the patient.

More specifically, the boost circuit of the iontophoresis system includes an inductor L2 which is selectively coupled across the outputs of the power supply 20 when the first switching means 24 (i.e., switch S2) is in the conductive state. Energy from the power supply 20 is transferred to the inductor L2 when the first switching means is conductive.

The circuit also includes a diode D2 which acts as the second switching means 28. The diode D2 has its anode connected to the junction of one pole of the switch S2 and the inductor L2, and its cathode connected to the positive electrode 8 of the transdermal drug delivery device 2. Also, a capacitor C2 for filtering out ripple may be included and connected in parallel with the electrodes 6, 8 of the drug delivery device, with the negative electrode 6 also being connected to the other pole of the switch S2 and the negative output of the power supply 20.

After the inductor L2 has charged, the first switching means (switch S2) is opened by the control circuit 26. The inductor discharges through the diode D2 and transfers its energy to the transdermal drug delivery device, driving the ionic medication into the skin and tissue of the patient. Accordingly, only a packet of energy which is stored in the inductor L2 is transferred to the drug delivery device. It should be noted that the arrangement of the components of the boost circuit shown in FIG. 4 is slightly different from the block diagram illustrated by FIG. 1 in that the position of the first switching means (i.e., switch S2) and inductor L2 (i.e., the storage device 22) are reversed. However, the circuits function similarly by causing power from the supply to be transferred to and stored in the storage device and the stored power is later transferred to the electrodes of the drug delivery device.

Should a component fail in the circuit described above, the voltage V provided to the electrodes of the transdermal drug delivery device 2 will decrease to be less than or equal to the power supply voltage E. The power supply voltage E is, as mentioned previously, selected to be at a safe level which will prevent burns and damage to the patient's skin.

More specifically, if the capacitor C2 fails and appears as an open circuit, more voltage ripple will be present on the electrodes but still only the energy stored in the inductor L2 will be delivered to the transdermal drug delivery device. If the capacitor C2 fails as a short circuit, the electrodes 6,8 of the drug delivery device are shorted and no current flows through the patient's skin.

If the diode D2 fails as an open circuit, no current or voltage is provided to the transdermal drug delivery device. If the diode fails as a short circuit, the output voltage V on the electrodes will be effectively O volts when the first switching means 24 (switch S2) closes, and equal to voltage V when the first switching means opens and the inductor L2 discharges. Accordingly, the average voltage supplied to the electrodes will be at a predetermined safe level between voltages E and V.

If the first switching means 24 (i.e., switch S2) fails as an open circuit, the inductor L2 will charge and effectively act as a short circuit and the voltage V delivered to the drug delivery device will substantially equal the safe power supply voltage E. If the switch S2 fails as a short circuit, the diode D2 will never be forward biased and the output voltage V provided to the electrodes of the transdermal drug delivery device will be zero.

If the inductor L2 fails as an open circuit, no energy will be transferred from the power supply 20 to the transdermal drug delivery device 2. If the inductor fails as a short circuit, the output voltage V across the electrodes of the transdermal drug delivery device will be approximately equal to the average between the power supply voltage E (when the first switching means opens) and O volts (when the first switching means closes).

Figure 5:
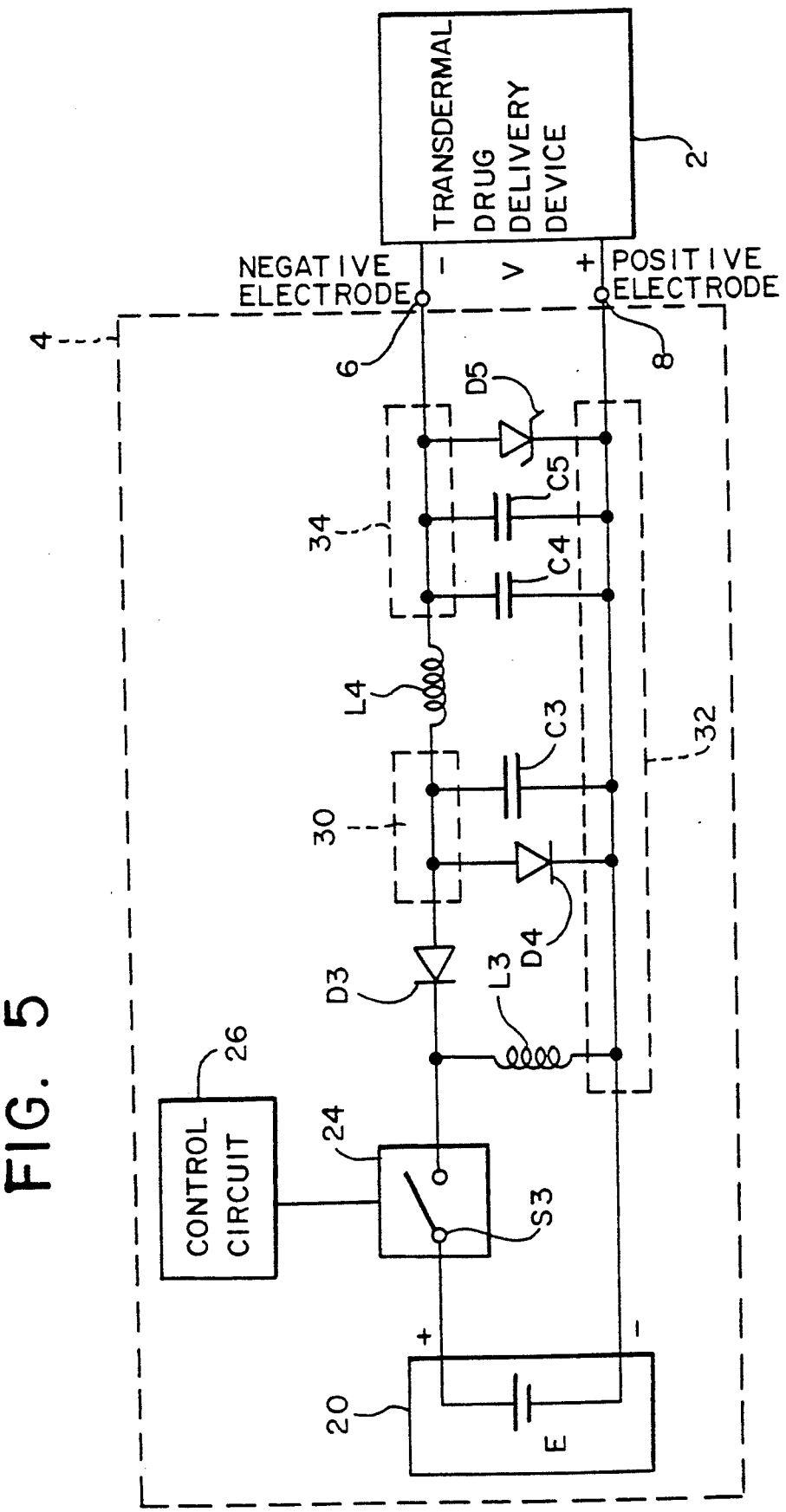
FIG. 5 is a schematic diagram of a third embodiment of an iontophoresis system formed in accordance with the present invention.

FIG. 5 illustrates a third embodiment of the iontophoresis system of the present invention. The transdermal drug delivery device 2 is connected to the current and voltage delivery circuit 4 as shown in FIG. 5. The current and voltage delivery circuit 4 as shown in FIG. 5 is a buck-boost circuit similar to the buck-boost circuit shown in FIG. 3 and as described above. However, the present embodiment differs from that of FIG. 3 in that the circuit of FIG. 5 is provided with additional ripple filtering means and output protection means in view of the potential for malfunction of circuit elements.

As shown in FIG. 5, an inductor L3 has a first end coupled to switch S3 and a second end coupled to a node 32. A power supply 20 generates a voltage E which is provided across inductor L3. L3 acts as the intermediary storage device 22 when an electronically controlled single pole, single throw (SPST) switch S3 (which acts as the first switching means 24) is activated to be conductive by the control circuit 26. The energy provided by the power supply 20 is transferred to and stored in the inductor L3.

A diode D3 functions as the second switching means 28. The diode D3 has its cathode end connected to the inductor L3 on the positive side of the power supply 20. The anode end of diode D3 is connected to the anode end of a second diode D4 at a second node 30. Diode D4 will act as a short under certain conditions within the voltage delivery circuit 4 in order to prevent node 30 from going positive. More specifically, if diode D3 shorts, the circuit will try to drive the negative electrode positive. Diode D4 effectively clamps the negative electrode from going positive. This provides added protection for the circuit. The cathode of diode D4 is coupled to node 32.

Also coupled to node 30, which electrically connects the anodes of diodes D3 and D4, is a first end of a capacitor C3 and a first end of an inductor L4. The second end of inductor L4 is coupled to a first end of a capacitor C4 at a third node 34, effectively forming a $\pi$ filter section which removes most ripple or transients from the signal provided to the transdermal drug delivery device 2. The second end of capacitor C3 and the second end of capacitor C4 are coupled to node 32. Also, a capacitor C5 having a capacitance that is smaller in value than capacitor C4 but having a greater frequency response is connected in parallel across capacitor C4. In this manner, the $\pi$ filter section with capacitors C4 and C5 reduce any transients or ripple in the voltage supplied to the electrodes of the drug delivery device.

A zener diode D5 having an anode end and a cathode end is connected at its anode end to the negative (cathode) electrode 6 of the transdermal drug delivery device 2 and to node 34, which also connects inductor L4 and capacitors C4 and C5. The cathode end of zener diode D5 is coupled to node 32. All of the above-identified components connected to node 32 are coupled to the positive (anode) electrode 8. The zener diode D5 ensures that the voltage provided to the electrodes does not exceed a predetermined voltage level.

The operation of the iontophoresis system shown in FIG. 5 will now be described.

When the transdermal drug delivery device 2 is coupled to the current and voltage delivery circuit 4 at electrodes 6, 8, switch S3 is thrown by control circuit 26 and the energy is provided from the power supply 20 to the inductor L3. The diode D3 is back biased so that no current is provided to the rest of the circuit including the filter section comprising capacitors C3, C4, C5 and inductor L4, zener-regulator diode D5 or the electrodes of the transdermal drug delivery device 2.

After the inductor has been energized, the control circuit 26 causes switch S3 (i.e., the first switching means 24) to open. Thereafter, the field induced by the voltage impressed across the inductor L3 collapses, causing a current to flow through inductor L3 and forward biasing the diode D3. The forward biased diode D3 allows a current to flow through the $\pi$ filter section and electrodes 6, 8. In addition, a voltage V is impressed across the electrodes of the transdermal drug delivery device 2 until all or part of the energy which had been stored in the inductor L3 has been dissipated to the transdermal drug delivery device 2. After the inductor L3 has discharged, current will cease flowing through the electrodes 6, 8 of the drug delivery device. Thereafter, the SPST switch S3 is periodically activated to connect the voltage source 20 to inductor L3.

In addition to the advantages mentioned above with respect to the embodiment depicted in FIG. 3, the advantage of the iontophoresis system of the present embodiment is that if diode D3 malfunctions and is shorted, the negative (cathode) electrode 6 of the transdermal drug delivery device 2 will be prevented from going positive. Also, the filtering section comprising capacitors C3, C4 and inductor L4 (which section is configured as a $\pi$ filter) provides for a smoother DC output and therefore more efficient use of the energy stored and released from the supply 20.

To facilitate an understanding of the invention, it should be noted that in the embodiments described previously, the diodes are considered ideal devices with no voltage drop. Also, for a 6 volt power supply (i.e., E=6 volts), the preferred values of the components shown in FIG. 5 are the following: inductor L3=390 $\mu$H; inductor L4=82 $\mu$H; capacitor C4=10 $\mu$f; capacitor C5=0.01 $\mu$f; diode D5=16 volt zener diode; and diodes D3 and D4 are Part Nos. BAS40 manufactured by Siemens Components, Inc. in Iselin, N.J.

Figure 6:
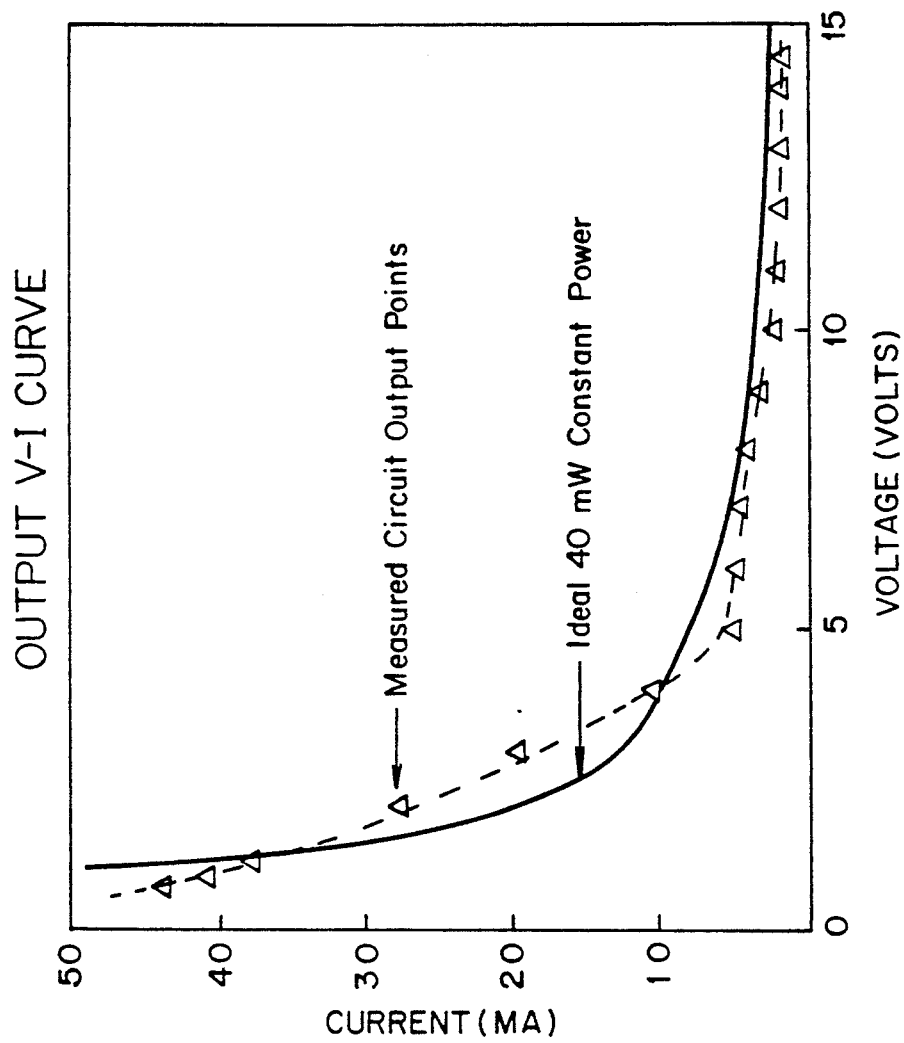
FIG. 6 is a graph plotting the ideal and measured output voltage/current curves for the circuit shown in FIG. 5.

FIG. 6 is a graph depicting an ideal voltage/current curve for a constant 40 mW power provided to the transdermal drug delivery system and the measured output voltage/current curve for the circuit shown in FIG. 5. A constant power with the fail-safe capabilities described previously is what is desired for the iontophoresis system of the present invention, and the actual constant power limitation, which closely follows the ideal curve, is what is achieved using the circuit shown in FIG. 5. It should be noted that a constant power provided to the electrodes of the transdermal drug delivery device is achieved without feedback, that is, without the need to monitor the voltage or current provided to the electrodes.

As described in detail previously, the iontophoresis system of the present invention is failsafe in that a controlled amount of energy, in the form of a voltage or current, is provided to the transdermal drug delivery device. Specifically, under normal operation the power supply is not connected directly to the transdermal drug delivery device 2. Therefore, if a failure occurs in one of the components, only the controlled and predetermined quantity of energy stored in the storage device, i.e., inductor L3, used in the system is delivered to the transdermal drug delivery device. Therefore, the voltage provided to the electrodes of the transdermal drug delivery device decreases from an initial safe level to a predetermined level so that damage or burns to the patient's skin may be avoided.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An iontophoresis system, which comprises:
    an iontophoretic drug delivery device for placement against the skin of a patient, the drug delivery device including:
    a first electrode;
    means for holding an electrolyte situated in relation to the first electrode such that an electrolyte held by the electrolyte holding means is in electrical communication with the first electrode;
    a second electrode; and
    means for holding an ionic medication situated in relation to the second electrode such that an ionic medication held by the medication holding means is in electrical communication with the second electrode; and
    a circuit for controlling the current or voltage provided to the electrodes of the drug delivery device, the circuit including:
    first switching means, the first switching means being coupled to a source of power, the first switching means having a conductive state and a non-conductive state;

control means coupled to the first switching means for causing the first switching means to be in one of the conductive state and the non-conductive state;

an intermediary storage device, the intermediary storage device being coupled to the first switching means such that energy from the power source is transferred to and stored in the intermediary storage device when the first switching means is in the conductive state; and second switching means, the second switching means being coupled between the intermediary storage device and the electrodes of the drug delivery device, the second switching means selectively coupling the intermediary storage device to the drug delivery device wherein when the first switching means is in the conductive state, the second switching means effectively decouples the intermediary storage device from the electrodes of the drug delivery device and wherein when the first switching means is in the non-conductive state, the second switching means effectively couples the intermediary storage device to the electrodes of the drug delivery device allowing energy stored in the intermediary storage device to be transferred to the drug delivery device thereby providing sufficient power to cause the ionic medication to be driven into the skin of a patient.

2. An iontophoresis system as defined by claim 1, wherein the intermediary storage device includes an inductor, and the second switching means includes a diode.

3. An iontophoresis system having an iontophoretic drug delivery device for placement against the skin of a patient, which comprises:

a power source for generating a current and voltage; and a circuit coupled between the power source and the drug delivery device for delivering current and voltage form the power source to the drug delivery device, the circuit including a plurality of components; and means for one of interrupting the power or maintaining the power at least equal to a predetermined level if one of the power source or circuit components fail to one of an open circuit and a short circuit, thereby effectively preventing burns, shocks, and other dangerous effects caused by excessive current and voltage being applied to the skin of a patient.

4. A circuit for use in an iontophoresis system having an iontophoretic drug delivery device for placement against the skin of a patient, the iontophoretic drug delivery device having a positive electrode and a negative electrode and the iontophoresis system including a power source for generating a current and voltage, the circuit comprising:

first switching means, the first switching means being coupled to the power source of the iontophoresis system, the first switching means having a conductive state and a non-conductive state;

control means coupled to the first switching means for causing the first switching means to be in one of the conductive state and the non-conductive state;

an inductor, the inductor being coupled to the first switching means such that energy from the power source is transferred to and stored in the inductor when the first switching means is in the conductive state; and a diode, the diode being coupled between the inductor and at least one of the electrodes of the iontophoretic drug delivery device, the diode selectively coupling the inductor to the at least one electrode of the drug delivery device, wherein when the first switching means is in the conductive state, the diode effectively decouples the inductor from the electrodes and, wherein when the first switching means is in the non-conductive state, the diode effectively couples the inductor to the electrodes to allow energy stored in the inductor to be transferred to the drug delivery device thereby providing sufficient power to cause an ionic medication to be driven into the skin of the patient.

5. A circuit as defined by claim 4, which further includes a capacitor, the capacitor being electrically coupled to the diode and further being coupled across the electrodes of the drug delivery device for filtering voltage ripple and voltage transients produced during the transfer of energy from the inductor to the electrodes of the drug delivery device.

6. A circuit for use in an iontophoresis system having an iontophoretic drug delivery device for placement against the skin of a patient, the iontophoretic drug delivery device having a positive electrode and a negative electrode and the iontophoresis system including a power source for generating a current and voltage, the circuit comprising:

a storage device, the storage device being coupled to the power source to allow energy from the power source to be stored therein;

first switching mans, the first switching means being coupled to the storage device and the power source to define with the power source and the storage device a current flow circuit for transferring energy from the power source to the storage device, the first switching means having a conductive state and a non-conductive state;

control means coupled to the first switching means for causing the first switching means to be in one of the conductive state and the non-conductive state; and second switching means, the second switching means being coupled to the first switching means and the storage device and at least one of the electrodes of the drug delivery device, the second switching means selectively coupling the storage device to one of the positive and negative electrode of the drug delivery device, wherein energy is transferred to and stored in the storage device from the power source when the first switching means is in the conductive state, and wherein the second switching means effectively decouples the storage device from the electrodes of the drug delivery device when the first switching means is in the conductive state; and wherein the second switching means effectively couples the storage device to the electrodes of the drug delivery device when the first switching means is in the non-conductive state thereby allowing energy stored in the storage device to be transferred to one of the positive and negative electrodes of the drug delivery device to cause an ionic medication to be driven into the skin of a patient.

7. A circuit as defined by claim 6, wherein the storage device includes an inductor, and the second switching means includes a diode.

8. A circuit for use in an iontophoresis system having an iontophoretic drug delivery device for placement against the skin of a patient, the iontophoresis drug delivery device having a positive electrode and a negative electrode and the iontophoresis system including a power source for generating a current and voltage, the circuit comprising:

first switching means, the first switching means being coupled to the power source, the first switching means having a conductive state and a non-conductive state;

control means coupled to the first switching means for causing the first switching means to be in one of the conductive state and the non-conductive state;

a first inductor, the first inductor being coupled to the first switching means such that energy from the power source is transferred to and stored in the first inductor when the first switching means is in the conductive state; and a first diode, the first diode having an anode end and a cathode end, the cathode end of the first diode being coupled to the first inductor;

a filtering section, the filtering section being coupled between the anode end of the first diode and to at least one of the electrodes of the drug delivery device, the first diode selectively coupling the first inductor to at least one electrode of the iontophoretic drug delivery device through the filtering section, wherein when the first switching means is in the conductive state, the diode effectively decouples the inductor from the electrodes and, wherein when the first switching means is in the non-conductive state, the diode effectively couples the inductor to the electrodes to allow energy stored in the first inductor to be transferred to the iontophoretic drug delivery device thereby providing sufficient power to cause an ionic medication to be driven into the skin of a patient.

9. A circuit as defined by claim 8, which further comprises a second diode, the second diode having an anode end and a cathode end, the anode end of the second diode being coupled to the anode end of the first diode.

10. A circuit as defined by claim 8, which further comprises a zener-regulator diode, the zener-regulator diode having an anode end and a cathode end, the anode end of the zener-regulator diode being coupled to the negative electrode and the cathode end of the zener-regulator diode being coupled to the positive electrode of the drug delivery device.

11. A circuit as defined by claim 8, wherein the filtering section is formed as a $\pi$ filter and includes an first capacitor having a first end coupled to the anode of the first diode and a second end coupled to the positive electrode, a second inductor having first and second ends, the first end of the second inductor being coupled to the anode of the first diode and the second end of the second inductor being coupled to the negative electrode of the drug delivery device, and a second capacitor coupled across the positive and negative electrodes of the drug delivery device.

12. A circuit for use in an iontophoresis system having an iontophoretic drug delivery device for placement against the skin of a patient, the iontophoresis drug delivery device having a positive electrode and a negative electrode and the iontophoresis system including a power source for generating a current and voltage, the circuit comprising:

a storage device, the storage device being coupled to the power source to allow energy from the power source to be stored therein;

first switching means, the first switching means being coupled to the storage device and the power source to define with the power source and the storage device a current flow circuit for transferring energy from the power source to the storage device, the first switching means having a conductive state and a non-conductive state;

control means coupled to the first switching means for causing the first switching means to be in one of the conductive state and the non-conductive state, wherein energy is transferred to and stored in the storage device from the power source when the first switching means is in the conductive state;

second switching means, the second switching means being coupled to the first switching means and to the storage device;

a filter circuit, the filter circuit being coupled to the second switching means, the second switching means selectively coupling the storage device to one of the positive and negative electrode of the drug delivery device through the filter circuit, wherein energy is transferred to and stored in the storage device from the power source when the first switching means is in the conductive state, and wherein the second switching means effectively decouples the storage device from the electrodes of the drug delivery device when the first switching means is in the conductive state, and wherein the second switching means effectively couples the storage device to the electrodes of the drug delivery device when the first switching means is in the non-conductive state thereby allowing energy stored in the storage device to be transferred to one of the positive and negative electrode of the drug delivery device to cause an ionic medication to be driven into the skin of a patient.

13. A circuit as defined by claim 12, wherein the storage device includes an inductor, and the second switching means includes at least a first diode.

14. A circuit as defined by claim 12, which further comprises a voltage clamping circuit, the voltage clamping circuit being electrically coupled to at least one of the electrodes.

15. A circuit as defined by claim 12, which further comprises a voltage regulating circuit, the voltage regulating circuit being coupled across the positive and negative electrodes of the drug delivery device.

16. A method for delivering and controlling energy provided to an iontophoretic drug delivery device, the drug delivery device including a power source, a storage device coupled to the power source and a pair of electrodes on the drug delivery device coupled to the storage device, the method comprising the steps of:

coupling the power source to the storage device, said storage device being uncoupled from said electrodes while said power source and storage device are coupled thereby permitting the transfer of energy from the power source to the storage device; and uncoupling the power source from the storage device, said storage device being coupled to said electrodes while said power source and storage device are uncoupled, said storage device thereby providing energy to the iontophoretic drug delivery device to drive ionic medication into the skin of a patient.

17. A method as defined by claim 16, which further comprises the step of:
   filtering the energy transferred from the storage device to the electrodes of the drug delivery device thereby reducing voltage ripple and transients.

18. A method for delivering and controlling energy provided to power an iontophoretic drug delivery device having an ionic medication thereon and a positive electrode and a negative electrode, the iontophoresis system including a power source for generating a current and voltage, the iontophoresis system further including a circuit having: a storage device, the storage device being coupled to the power source to allow energy from the power source to be stored therein, first switching means, the first switching means being coupled to the storage device, the first switching means having a conductive state and a non-conductive state, and second switching means, the second switching means being coupled to the storage device and at least one of the electrodes of the iontophoretic drug delivery device, the second switching means having a conductive state and a non-conductive state, the method comprising the steps of:
   switching the first switching means into said conductive state thereby transferring energy from the power source to the storage device while said second switching means is effectively in the non-conductive state; and
   switching the first switching means into said non-conductive state thereby disconnecting the power source from the storage device while said second switching means is effectively in the conductive state thereby transferring energy from the storage device to the electrodes of the iontophoretic drug delivery device thus driving the ionic medication into a patient's skin.

19. A method as defined by claim 8, which further comprises the step of:
   filtering the energy transferred from the storage device to the at least one of the electrodes of the iontophoretic drug delivery device thereby reducing voltage ripple and transients.

* * * * *